US006214014B1

(12) United States Patent
McGann

(10) Patent No.: US 6,214,014 B1
(45) Date of Patent: Apr. 10, 2001

(54) ACETABULAR TOTAL HIP COMPONENT ALIGNMENT SYSTEM FOR ACCURATE INTRAOPERATIVE POSITIONING IN INCLINATION

(76) Inventor: William A. McGann, 55 20th Ave., San Francisco, CA (US) 94121

( * ) Notice: Subject to any disclaimer, the term of this patent is extended or adjusted under 35 U.S.C. 154(b) by 0 days.

(21) Appl. No.: 09/314,699

(22) Filed: May 19, 1999

Related U.S. Application Data

(60) Provisional application No. 60/086,031, filed on May 19, 1998.

(51) Int. Cl.[7] ................................................ A61B 17/56
(52) U.S. Cl. ............................................. 606/102; 606/91
(58) Field of Search ............................... 606/87, 88, 89, 606/90, 91, 102; 623/19–23; 128/777; 33/228, 511; 356/253; 364/561

(56) References Cited

U.S. PATENT DOCUMENTS 5,007,936 * 4/1991 Woolson ................................ 623/23
5,037,424    8/1991 Aboczsky ............................. 606/91
5,141,512    8/1992 Farmer et al. ....................... 606/87
5,413,116 * 5/1995 Radke et al. ........................ 128/777
5,527,317 * 6/1996 Ashby et al. ........................ 606/91
5,700,268 * 12/1997 Bertin .................................. 606/102
5,832,422 * 11/1998 Wiendenhoefer ................... 364/561
5,870,832 * 2/1999 Slocum ................................ 33/511
5,961,555 * 10/1999 Huebner .............................. 623/19

OTHER PUBLICATIONS

PCT Notification of Transmittal of the International Search Report or the Declaration for PCT/US99/10990, Int'l Filing Date May 19, 1999, mailed Oct. 26, 1999. (Now Public Document WO/9959487.

* cited by examiner

Primary Examiner—David O. Reip
(74) Attorney, Agent, or Firm—Fliesler, Dubb, Meyer & Lovejoy

(57) ABSTRACT

An alignment system 20 is used for alignment structure for surgical procedures. The alignment system and method can be used in a preferred embodiment to align an acetabular cup implant for purposes of a hip replacement procedure. The alignment system and method can be used for other alignment procedures whether or not an implant is utilized.

6 Claims, 4 Drawing Sheets

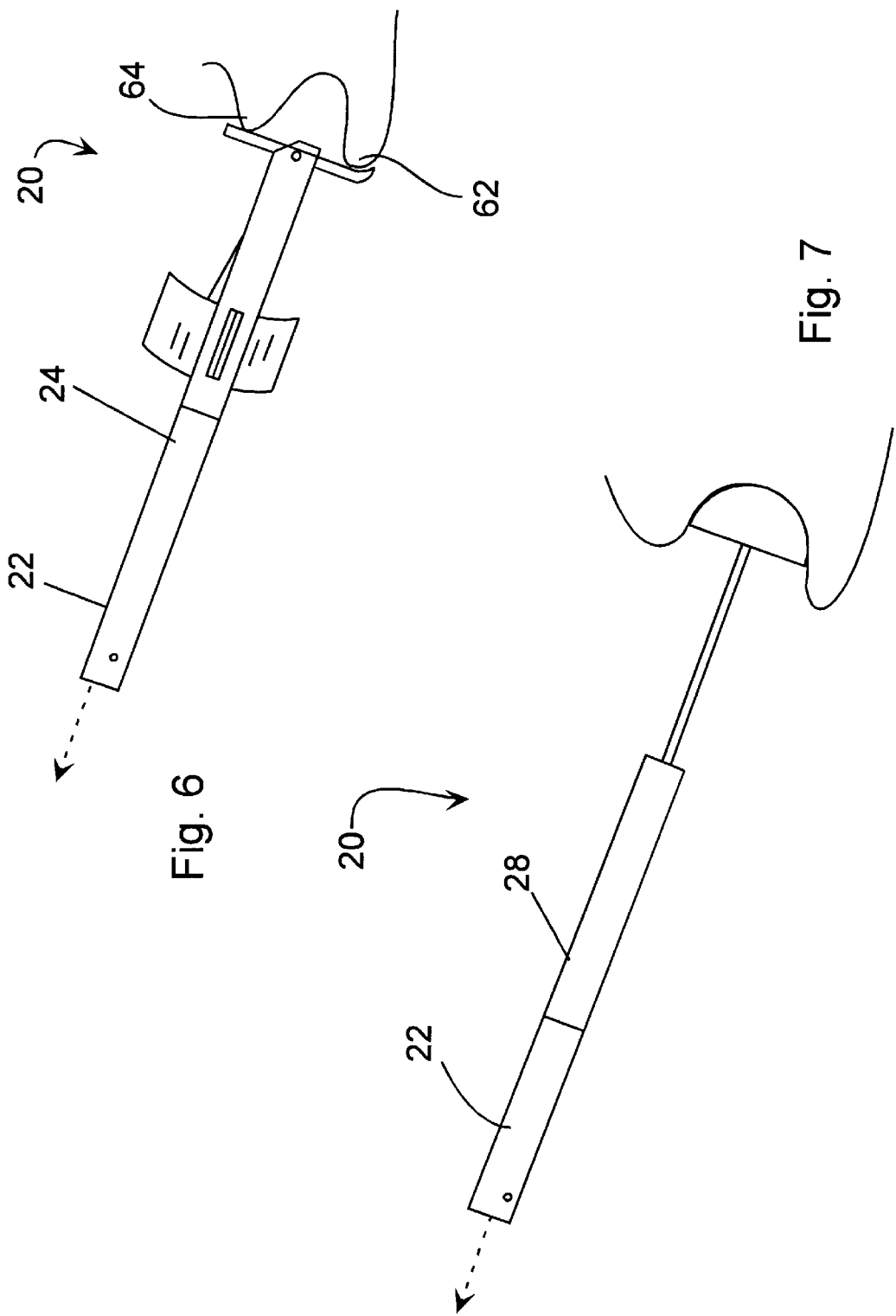

ACETABULAR TOTAL HIP COMPONENT ALIGNMENT SYSTEM FOR ACCURATE INTRAOPERATIVE POSITIONING IN INCLINATION

The application claims the benefit of U.S. Provisional Application Ser. No. 60/086,031, filed May 19, 1998.

FIELD OF THE INVENTION

The present invention is directed to systems which aid alignment during surgical procedures. Such systems can be used with procedures which perform surgeries on anatomical features with or without the positioning of an implant.

BACKGROUND OF THE INVENTION

Total hip replacement surgery requires accurate positioning of the acetabular and femoral components during the actual surgery. The acetabular component, sometimes referred to as the "socket" is aligned to the pelvis three dimensionally. Surgeons tend to orient the socket in terms of two dimensions. These two dimensions are termed anteversion, and inclination. Anteversion is the forward tilt of the axis of the hemispherical socket. Inclination is the upward tilt of the component. FIG. 1 depicts the inclination angle A in a front view of the pelvis. FIG. 2 depicts the anteversion angle B in a bottom view of the pelvis.

In anatomic terms, the anteversion is forward towards the front of the patient in the transverse plane. Inclination is in an upward direction in the coronal plane.

These two positions, anteversion and inclination can be critical to the stability of the total hip replacement. If the socket is placed either under or over certain angles, the hip will be unstable, and will dislocate. Dislocation usually requires an emergency transfer of the patient to a medical facility where anesthetics are administered and the hip manipulated back into place. Generally, the hip can be reduced or correctly positioned by closed means. However, in some cases, the patient may require an emergency operation to openly reduce or correctly position the hip joint. The degree of desired anteversion and inclination varies between surgeons, and there is no absolute value that is universally agreed upon. Clinical studies of dislocated prostheses show a significant extreme in the angular placement of the socket. In fact, the most common cause of dislocation that is due to component malposition is a malpositioned socket. Either under anteversion, retroversion (the plane of the socket is less than zero), or occasionally over anteversion can all lead to unstable replacements. If the inclination is above 60 degrees from the horizontal axis, there is a statistically increased risk of dislocation. Most surgeons report the ideal position of a socket at between 15 and 20 degrees of anteversion, and 40 to 45 degrees of inclination. When surgeons err, they prefer to place the socket with more anteversion, rather than less, and less inclination rather than more.

Anteversion is easier to estimate than inclination since there are more landmarks to reference. In the lower portion of the acetabulum, there is a ligament termed the transverse acetabular ligament. It has been described as a reference that can be used to determine anteversion. The surgeon more commonly estimates anteversion simply by referencing the coronal plane of the patient. Since the torso, shoulder, and pubis are generally visible or palpable, these landmarks can be utilized in the estimation of the coronal plane, and therefore the position of the socket in anteversion.

Inclination is much more difficult to assess than anteversion. The surgeon has few, if any, landmarks to spatially orient the pelvis in the sagittal plane. To rely on the visible bony anatomy of the acetabulum is misleading. The majority of acetabular are inclined steeper than 45 degrees. Attempting to use the rim of the acetabulum to orient inclination varies with the size of the acetabular socket. In addition, the pelvis is known to move in different directions during the operation. This makes it extremely difficult, if not impossible, to reference the pelvis during the insertion of the socket. Sophisticated electronic methods have been devised to track the position of the pelvis during surgery, but then can be expensive, invasive, and impractical for everyday use. Surgeons are left with a method of estimation of pelvis position to the horizontal plane. Manufacturers have provided guides that attempt to orient the socket to the horizontal plane. Some have even incorporated leveling devices to help orient the guide. However, all of these methods rely on the pelvis being oriented to that plane, a method that involves a crude estimation. Intraoperative radiographs have been described to confirm socket position, but have not been popular because of the impracticality of their use.

SUMMARY OF THE INVENTION

The present invention is directed to an alignment system for use in surgical procedures which may or may not include an implant. The alignment system and method in a particular embodiment depicted is used for aligning an acetabular socket for a hip replacement. It is to be understood that such an alignment system and method can be used for implanting other implants and also in situations where the natural structure such as bony structures of the patient must be aligned and contained in position with other tissues from the patient.

Accordingly, it is an object of the present invention to provide an alignment system comprising a reference adapted for positioning adjacent to an anatomical tissue and a device which can establish an angle relative to the reference.

A further object of the invention includes a surgical alignment system comprising a means for defining a reference which is adapted for positioning adjacent to an anatomical structure and means for establishing an angle relative to said means for defining a reference.

A further aspect of the present invention includes a method for establishing alignment for the implantation of a device comprising the steps of locating a landmark, using the landmark to position an alignment system, and using the alignment system to establish an alignment.

Other aspects, objects and advantages of the invention can be obtained from a review of the detailed description of the preferred embodiment, the figures, and the claims.

BRIEF DESCRIPTION OF THE FIGURES

FIG. 6 depicts a goniometer of FIG. 4 positioned adjacent the acetabular socket of a patient.

FIG. 7 depicts the insertion handle of FIG. 5 positioned in the acetabular socket of a patient.

DETAILED DESCRIPTION OF THE PREFERRED EMBODIMENT

Figure 3:
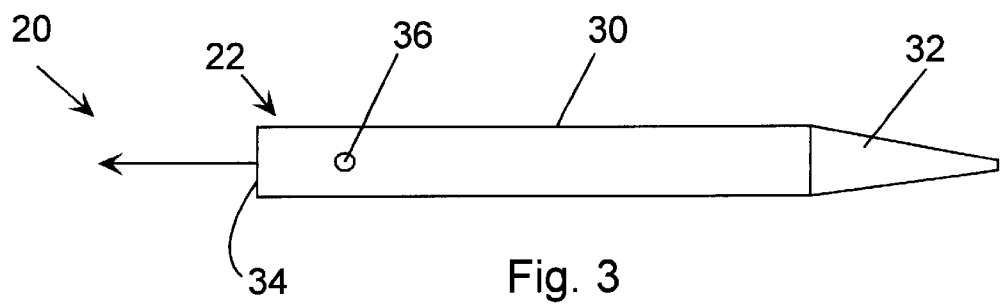
FIG. 3 depicts a plan view of an embodiment of a laser pointer or a laser torpedo of the alignment system of the invention.
Figure 4:
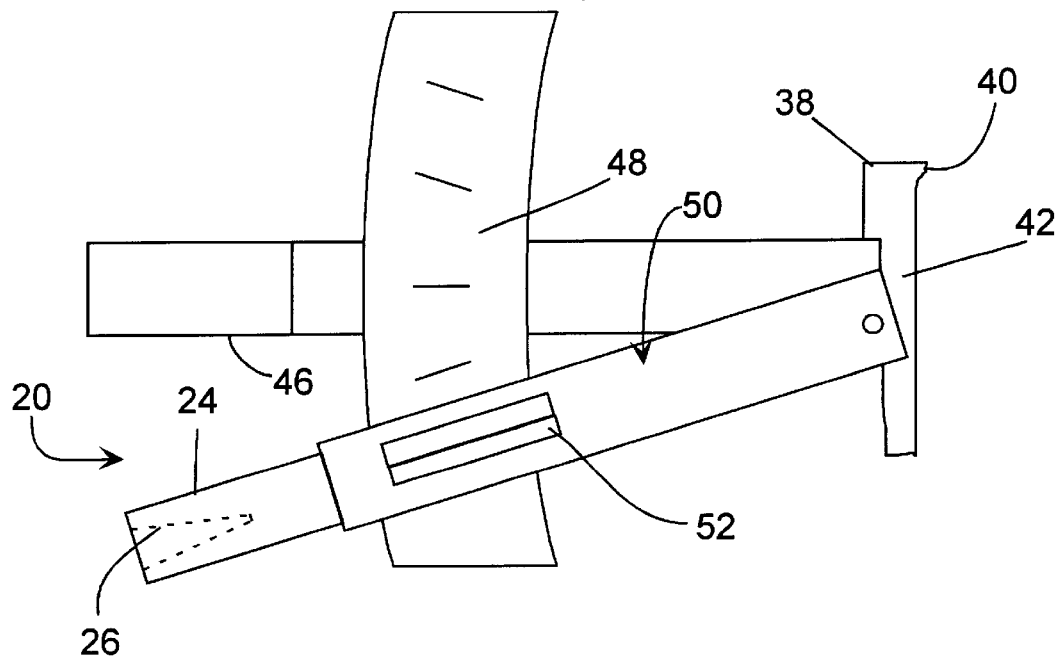
FIG. 4 depicts a plan view of an embodiment of a goniometer of the alignment system of the invention.
Figure 5:
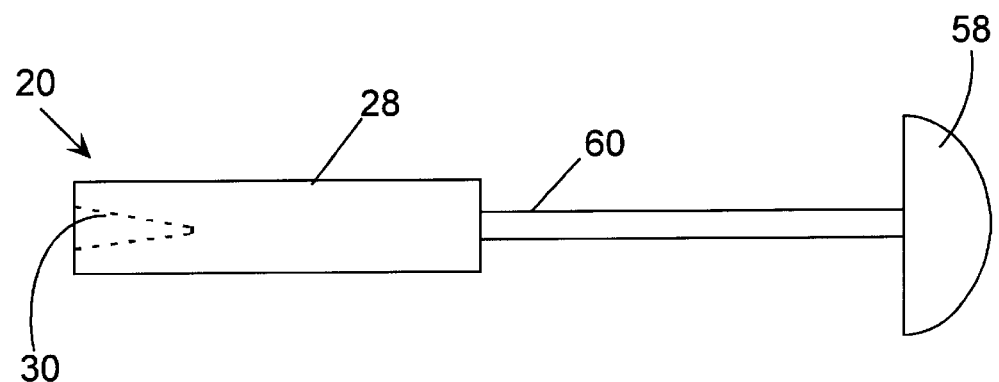
FIG. 5 depicts a plan view of an embodiment of an insertion handle of the alignment system of the invention.

The acetabular guide 20 of the invention, the components of which are shown in FIGS. 3, 4, and 5, is practical and accurate in positioning the prosthetic socket in the plane of inclination. The method estimates the actual inclination of the acetabulum and then references the final position of the acetabular component. The spatial reference is performed with the use of a laser pointer 22. The difference between the anatomic inclination of the acetabulum and the final inclination of the face of the acetabular component is an angular measurement that is compensated for via a goniometer 24. The goniometer 24 accepts the laser pointer 22 in bore 26, and the acetabular insertion handle 28 accepts the laser pointer 22 in bore 30. The surgeon then has a "target" (which is a point on the wall marked where the laser light indicated during a measurement with the goniometer 24), to aim at during the final insertion of the component. The position can be rechecked after insertion by re-aiming at the target. In revision operations (replacement of at least some component of a hip replacement system), the system 20 can also be utilized to determine the existing position of the socket, and incorporate any change that may be desired in the position of the new component. The laser beam 22 can create a target of either a point, or a line. A linear laser can project a line along the axis of the goniometer, so that the anteversion can be altered at the time of insertion of the acetabular component. A temporary, or permanent etching material may be utilized for the purpose of referencing the initial laser position.

The acetabular guide 20 in a preferred embodiment is comprised of the three components which are depicted in FIGS. 3, 4, and 5. In FIG. 3, the laser pointer 22 includes a housing 30 with a pointed end 32. Distally located from the pointed end 32 is a port 34 which accepts a laser light source, which can be actuated by button 36. The next component of the acetabular guide 20 includes the goniometer 24. Goniometer 24 includes a template 38 which includes a tab 40 and a flat reference 42. Secured to the template 38 is a first elongated body 46. Secured to the body 46 is a scale 48 which is used to measure the degree of offset desired. Pivotally pinned to the template 38 is a swing arm 50. Swing arm 50 includes a window 52 with an alignment guide 54 which is used to align the swing arm 50 relative to the scale 48. Located at the distal end of the swing arm 50 is the port 26 which accepts the laser pointer 22.

The third component of the acetabular guide 20 include the acetabular cup insert handle 28. Handle 28 includes as the first end, a semi-hemispherical body 58, which is formed to accept a prosthetic acetabular cup. Extending from the body 58 is a shaft 60, which at its distal end, includes an enlarged portion containing the bore 30 which accepts the laser pointer 22.

Figure 2:
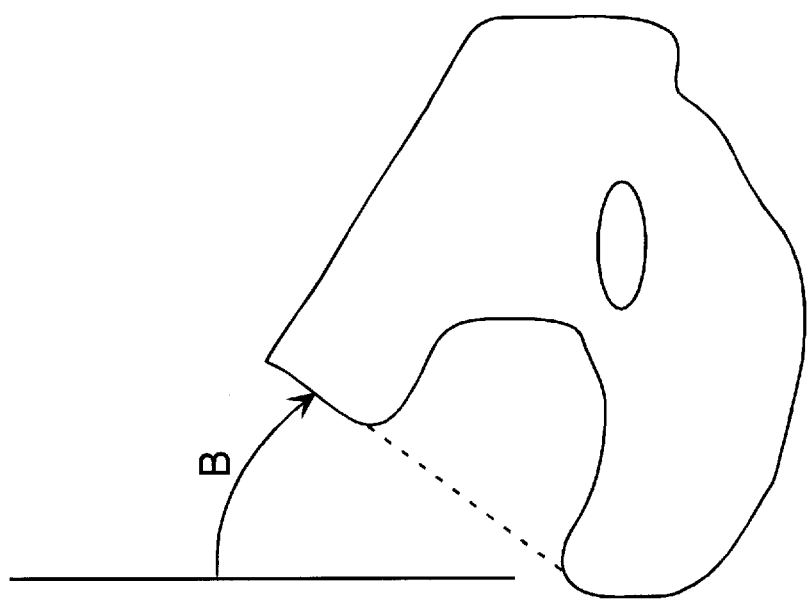
FIG. 2 depicts the anteversion angle B and a bottom view of the pelvis.
Figure 1:
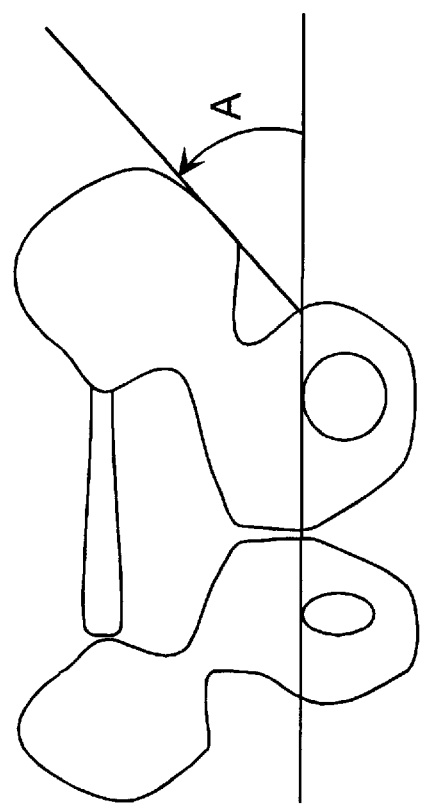
FIG. 1 depicts an inclination angle A and a front view of the pelvis.
Figure 8:
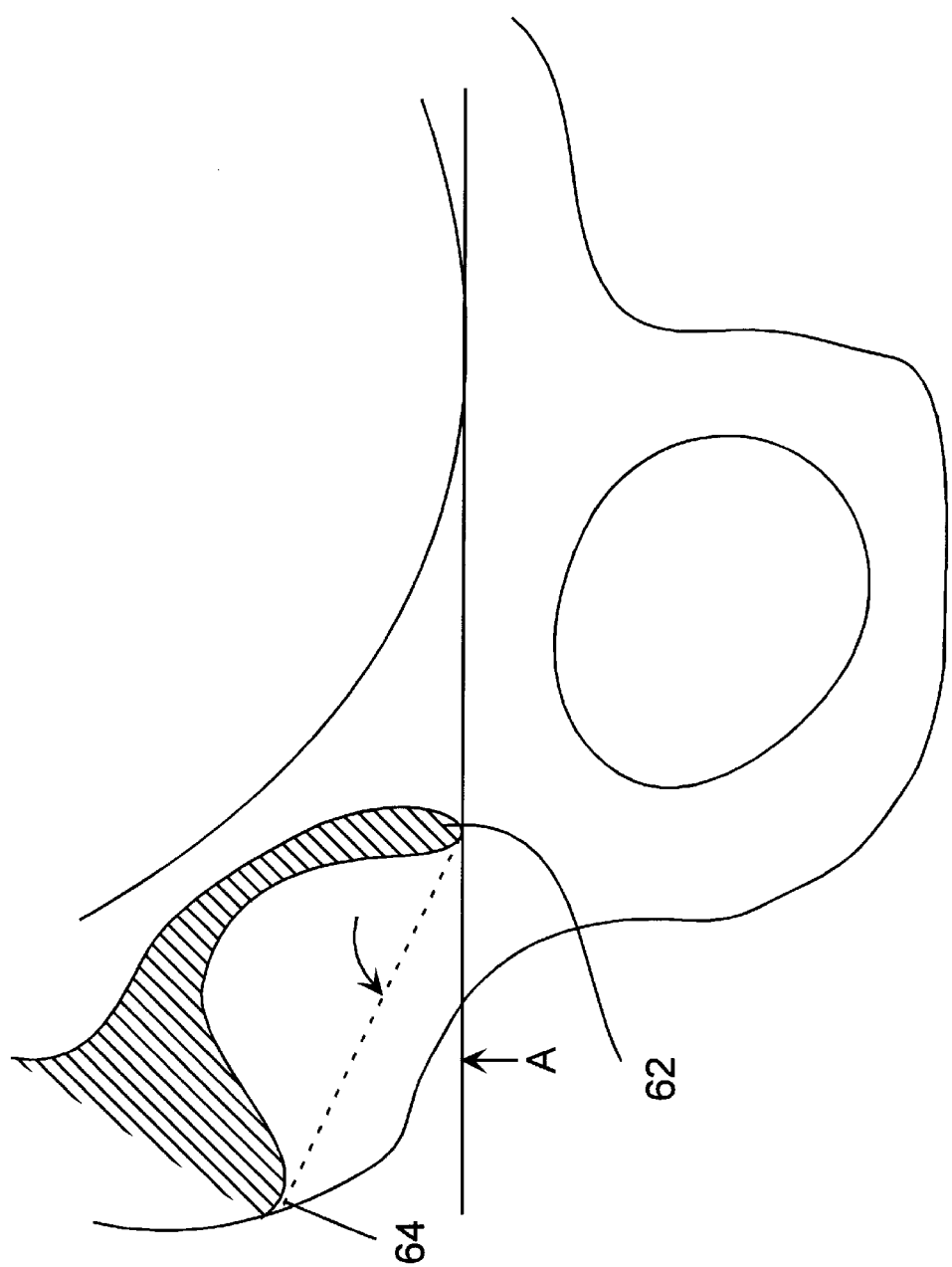
FIG. 8 depicts a portion of the pelvis of a patient which has been partially sectioned in order to show reference points used with the alignment system of the invention.

In operation, the acetabular guide 20 is used as follows. After the acetabular area of the patient is exposed, the template 38 of the goniometer is positioned adjacent the acetabular socket as is shown in FIG. 6. The template 38 is used to span from the teardrop location 62 as a first reference point seen in FIGS. 6 and 8 directly across to a second reference 64, which in a preferred embodiment is the lateral portion of the sourcil of an acetabular socket. The reference angle A is made relative to a line drawn between the teardrop structures of adjacent acetabular sockets as shown both in FIGS. 1 and 8.

After reference is positioned, the swing arm 50 of the goniometer is adjusted relative to the scale 48 for the desired offset. Once this is accomplished, the laser pointer 22 is inserted into the bore 26 and a mark is made on the wall where the laser light points. It is to be understood that this procedure occurs with the patient generally laying on his side. After the appropriate mark is indicated on the wall, the goniometer and laser pointer are removed and the prosthetic acetabular cup is inserted with the aid of the handle 28. The handle 28 is appropriately aligned by inserting the laser pointer 22 into the bore 30 and moving the handle 28 until the laser light of the laser pointer is aligned with the previously indicated mark on the wall. Once this has occurred, the acetabular cup is finally inserted into position. Thereafter, the alignment measurement is reconfirmed with the laser pointer 22 and the handle 28.

Industrial Applicability

Accordingly, the present invention provides for an alignment system which can be used for aligning various structures, and in a particular, various bony structures of a patient, whether or not an implant is associated with the surgical procedure. The invention includes the embodiment of the alignment system depicted as well as other embodiments. Further, the method of alignment using landmarks is also considered to be useful.

Other features, aspects and objects of the invention can be obtained from a review of the figures.

It is to be understood that other embodiments of the invention can be developed and fall within the spirit and scope of the invention.

I claim:

1. A surgical alignment system for hip replacement surgery comprising:
    a reference adapted for positioning adjacent to an anatomical tissue, which said reference has a first and second reference surface which are adapted for positioning adjacent to first and second bone landmarks respectively, which said first reference surface is shaped and adapted to mate with a teardrop anatomical structure of an acetabular socket;
    a device that can establish an angle relative to said reference, wherein said device includes a first body with a scale; and
    a second body which is pivotable relative to said reference in order to establish an angle relative to said scale.

2. The alignment system of claim 1 further including:
    a light source which is associated with one of the first body and the second body in order project a reference point in order to locate the position of the first body relative to the second body.

3. The alignment system of claim 1 wherein:
    said reference and said device comprise a goniometer and the system further including:
        a implant insertion handle which is adapted to hold an anatomical implant and can be aligned relative to anatomical tissue using the goniometer.

4. The alignment system of claim 3 including:
    a light source which is associated with said implant insertion handle in order to align said implant insertion handle with said goniometer.

5. The alignment system of claim 1 wherein:
    said reference is also positioned adjacent to the lateral sourcil structure of an acetabular socket.

6. A surgical alignment system for hip replacement surgery comprising:
    a means for defining a reference which is adapted for positioning adjacent to an anatomical structure, and said reference defining means has first and second reference surfaces which are adapted for positioning adjacent to first and second bone landmarks respectively, and which said first reference surface is shaped and is adapted to mate with a teardrop anatomical structure of an acetabular socket; and a means for establishing an angle relative to said means for defining a reference;

wherein said means for establishing an angle relative to the reference defining means includes:
a first body with a scale; and
a second body which is pivotable relative to said reference defining means in order to establish an angle relative to said first body.

* * * * *